US006410063B1

(12) United States Patent
Jewell et al.

(10) Patent No.: US 6,410,063 B1
(45) Date of Patent: Jun. 25, 2002

(54) COMPOSITION AND METHOD

(75) Inventors: Dennis Edward Jewell, Topeka; Claudia Ann Kirk, Lawrence; Philip William Toll, Valley Falls; Steven Curtis Zicker, Lawrence, all of KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 5 days.

(21) Appl. No.: 09/592,697

(22) Filed: Jun. 13, 2000

(51) Int. Cl.[7] .................................................. A23K 1/18
(52) U.S. Cl. ........................ 426/2; 426/601; 426/656; 426/661; 426/805
(58) Field of Search .......................... 426/2, 601, 656, 426/658, 661, 805

(56) References Cited

U.S. PATENT DOCUMENTS

| | | | | | |
|---|---|---|---|---|---|
| 6,013,622 | A | * | 1/2000 | Bruno et al. ................... | 514/2 |
| 6,203,825 | B1 | * | 3/2001 | Hodgkins ....................... | 426/2 |

FOREIGN PATENT DOCUMENTS

| | | | | |
|---|---|---|---|---|
| WO | 0004895 | 2/2000 | .......... | A61K/31/00 |
| WO | 0011964 | 3/2000 | ............ | A23K/1/16 |
| WO | WO 00/11964 | 3/2000 | | |
| WO | 0028985 | 5/2000 | .......... | A61K/31/19 |

OTHER PUBLICATIONS

Moser, Compendium on Cont. Edu. for the Practicing Verterinarian, vol. 13, No. 4, pp. 607–611, 1991.*

Kinsmann SL, Vinv EPG Quasky SA, Mellits ED, Freeman JM. Efficacy of the ketogenic diet for intractable seizure disorders: a review of 58 cases. Epilepsia 1992;33: 1132–1136.

Schwartz RH, Eaton J, Bower BD, AynsleyGreen A. Ketogenic diets in the treatment of epilepsy: short–term clinical effects. Dev Med Child Neurol 1989;31:145–151.

Schwartz RM, Boyes s, AnynsleyGreen A. Metabolic effects of three ketogenic diets in the treatment of severe epilepsy. Dev Med Child Neurol 1989;31:152–160.

Phelps SJ, Hovinga CA, Rose DF, Vaughn RD Olsen –Creasy K. The ketogenic diet in pediatric epilepsy. Nutrition in Clinical Practice 1998;13;267–281.

Wiener R, Hirsch HJ, Spitzer JJ. Cerebral extraction of ketones and their penetration into CSF in the dog. American Journal of Physiology 1971;220:1542–1546.

Withrow CD. Antipliliptic drugs. The ketogenic diet; Mechanisms of action. New York: Raven Press, 1980:635–642.

Appleton DB, De vivio DC. An animal model for the ketogenic diet. Electroconvulsive threshold and biochemical alterations consequent upon high–fat diet. Epilepsia 1974; 15:211–227.

Mahoney AW, Hendricks DG, Bernhard N, Sisson DV. Fasting and ketogenic diet effects on audoigenic seizure susceptibility in magnesium deficients rats. Pharmacol Biochem Behav 1983;18:683–687.

De Bruijne JJ. Biochemical observations during total starvation in dogs. International Journal of Obesity (1979) 3:239–247.

De Bruijne JJ, Altszuler N, Hampshire J, Vasser TJ,. Hackeng WHL. Fat Mobilization and Plasma Hormone Levels in Fasted Dogs. Metabolism, vol. 30, No. , (Feb. 1981).

Hematological and metabolic responses to training in racing sled dogs fed diets containing medium, low, or zero carbohydrate. DS Kronfeld et al., Am. Journ. of Clin. Nutrition, 30, 3, pp. 419–430 1977.

Isoenergetic substitution of dietary fat (beef tallow) for carbohydrates (cooked corn starch plus dextrin) does not affect magnesium absorption in cats. AC Beynen, J. Anim. Physiol. and Anim. Nutr., 72, 4/5 (1994) pp. 176–183.

Experimental research on aetiopathogenesis and diagnosis of ketotic hypoglycaemia syndrome in pregnant bitches. G. Polakowska–Nowak, Rozprawy I Monografie/Dissertations and Monographs, No. 10, 1999 (Abstract).

Effects of Dietary Carbohydrate, Fat and Protein on Growth, Body Composition and Blood Metabolite Levels in the Dog. D. R. Romos et al., J. of Nutrition, vol. 106, No. 10, 1976, pp. 1452–1464.

Ketogenic diet reduces spontaneous seizures and mossy fiber sprouting in the kainic acid model. AB Muller –Schwarz et al., Neuroreport, vol. 10, No. 7, 1999, pp. 1517–1522.

Macronutrient Intake and Obesity, JW Daily et al., J. Food Sci, Nutr., vol. 5, No. 1, pp. 58–64.

* cited by examiner

*Primary Examiner*—C Sayala
(74) *Attorney, Agent, or Firm*—Martin B. Barancik

(57) ABSTRACT

A diet which induces a state of ketosis in a canine or feline which comprises an edible composition relatively high in fats and relatively low in carbohydrates.

11 Claims, No Drawings

COMPOSITION AND METHOD

BACKGROUND OF THE INVENTION

Diet has been used in an attempt to manage conditions in man for many years. Obesity is often times directly related to the total and type of caloric intake for man over a given period of time. Diabetes first line of control is usually an attempt at management through diet. Similarly an attempt to limit high cholesterol values, hypertension, and urinary stone formation is frequently attempted by diet. In man, it has additionally been observed that a diet, which brings about a state of ketosis, that is increased ketone bodies, has met with some success in controlling the seizures associated with epilepsy.

In lower mammals, such as dogs, experiments to create a state of ketosis through the use of starvation has met with only limited attainment, J. J. de Bruijne, International Journal of Obesity (1979) 3, 239–247, see a further study on prolonged fasting in dogs by J. J. de Bruline, Metabolism (1981) Vol. 30, no. 2, 190–194. No ketotic state has been reported to have been achieved for a dog through use of a designed diet that uses a relatively high fat level combined with a relatively low carbohydrate level. The same lack of information concerning felines and lack of attainment of ketosis through use of diet, complete in all nutrients, is also present.

It has now been discovered that a state of ketosis can be achieved in lower mammals through the use of diet, in general a diet that is relatively high in fat and relatively low in carbohydrates. This alteration of metabolism, ketosis, can be useful in the management of various medical or behavioral conditions including but not limited to seizures, more specifically those related to idiopathic epilepsy; body weight regulation; behavior problems; muscle metabolism; carbohydrate intolerance; disorders of insulin secretion or insulin deficiency; muscle fatigue; suboptimal exercise tolerance and a combination of any of these conditions. In addition, alterations in metabolism and ketosis can enhance exercise performance.

SUMMARY OF THE INVENTION

In accordance there is a diet capable of inducing a state of ketosis in a dog or cat when fed the said diet on a regular basis, said diet comprising:

DOG

Carbohydrate measured as nitrogen free extract of about Zero to about 20 wt % of the diet, protein of from about 25% to about 70 wt % of the diet, and fat of from about 20 wt % to about 70 wt % of the diet all on a dry matter basis.

CAT

Carbohydrate as measured as nitrogen free extract of about zero to about 20 wt % of the diet, protein of from about 25 to about 70 wt % of the diet, and fat of from about 20 to about 70 wt % of the diet, all on a dry matter basis.

A further aspect of the invention is a method of inducing a ketotic state in a dog or cat which comprises feeding the dog or cat a diet which is relatively high in fat and relatively low in carbohydrate.

A still further aspect of the invention is a method for managing a medical or behavioral condition selected from the group consisting of seizures (related to idiopathic epilepsy), body weight regulation, behavior problems, muscle metabolism, carbohydrate intolerance, disorders of insulin secretion or deficiency, muscle fatigue and suboptimal exercise tolerance; enhanced exercise performance; and, a combination of any of these conditions in a dog or cat in need of such management which comprises feeding the dog or cat a diet which induces ketosis.

DETAILED DESCRIPTION OF THE INVENTION

A diet that induces a ketotic state in dogs and cats has been found to be high in fats and low in carbohydrates. By a "ketotic state" is meant alteration of the mammal's metabolism so as to increase the quantity of ketone bodies to levels significantly above the norm achieved with standard diets. Example(s) of these ketone body markers include betahydroxybutyrate, acetoacetate, and acetone.

Such a ketotic state inducing diet provides a nutritious maintenance diet to a dog or a cat with the benefit of altering the metabolism of the animal to attain the production of higher quantities of ketone bodies. The quantities of the significant components for the dog diet, all measured as wt. % of the diet and on a dry matter basis are about 0 to about 20 wt % of carbohydrates as nitrogen free extract, preferably 0 to about 10 wt %; about 25 to about 70 wt % of protein, preferably about 25 to about 40 wt %; and about 25 to about 70 wt % of fat, preferably about 30 to about 60 wt %.

The quantities of the significant components for the cat diet, all measured as wt % of the diet and on a dry matter basis are about 0 to about 20 wt % of carbohydrates as nitrogen free extract, preferably 0 to about 10 wt %; about 25 to about 70 wt % of protein, preferably about 30 to about 60 wt %; and about 20 to about 70 wt % of fat, preferably about 30 to about 60 wt %. Additionally, each diet will contain sufficient minerals and vitamins to avoid nutritional deficiencies.

The diet-induced state of ketosis can be useful in the treatment of certain conditions, which are affected by this altered metabolism. Examples of such conditions include but are not limited to seizures, for example, seizures accompanying idiopathic epilepsy particularly in dogs; weight regulation such as weight loss, gain, or maintenance; behavior problems, for example aggression, obsessive-compulsive disorder, and separation anxiety; muscle metabolism causing weakness or fatigue; carbohydrate intolerance (high or low blood sugar) for example, manifested by disorders of insulin secretion or insulin deficiency such as type II diabetes, exercise ability as shown by increased performance; and suboptimal exercise tolerance, for example myopathies and fatigue.

Below are examples of the invention. These examples are intended to illustrate the broad concept of the invention and not unduly limit it.

EXAMPLE 1

Twelve dogs were tested in a crossover design experiment.

All dogs were fed a standard maintenance canine diet for 2 weeks prior to the experimental period. At the start of the experiment, all dogs were held off of food for 24–48 hours to induce ketosis. Following this food deprivation period the animals were split into two groups with one being fed standard dog food and the other fed the nutritionally complete experimental ketogenic diet. All foods were fed at approximately 75–85% of maintenance requirement of calories as determined in the prefeeding period.

The experimental diet was introduced over a 3-day period as follows:

Day 1=⅓ experimental: ⅔ standard
Day 2=⅔ experimental: ⅓ standard
Day 3=100% experimental diet Diet intervention was maintained for 2 weeks. A one-week washout period was allowed and the animals were crossed over and repeated in the above testing methodology. Response to diet was assessed by measurement of serum ketone bodies at pretest, post food deprivation period, and end of food intervention periods. Statistical analysis of the response showed that feeding the experimental diet significantly increased (P<0.05) the level of ketone bodies in the blood of dogs compared to controls.

One composition of the new diet comprises fat, protein, supplemental minerals and vitamins, without any digestible carbohydrates. A small amount of fiber is added to maintain stool consistency. The diet is formulated to meet the AAFCO recommendations for all nutrients. A standard pet food diet would consist of the above constituents but also include 30–60% digestible carbohydrates in addition to fat, protein, minerals and vitamins in AAFCO recommended levels.

The composition components of the ketogenic diet and the ordinary canine diet utilized in the experiment are below:

DIET COMPOSITION-STUDY 1

| COMPONENT[1] | ORDINARY CANINE DIET (% WT)[2] | KETOGENIC DIET[2] |
|---|---|---|
| Moisture | 12.1 | 3.7 |
| Protein | 24.9 | 26.5 |
| Fat | 15.4 | 56.6 |
| NFE | 53.2 | 5.8 |
| Crude Fiber | 1.7 | 3.5 |
| Ash | 4.7 | 7.4 |

[1]Diets include minerals and vitamins sufficient to meet daily requirements.
[2]All wt % is based on dry matter except moisture, which is % as fed.

Both diets were fed in an amount estimated to be 0.75× daily energy requirement during the treatment periods. Data were analyzed in a completely randomized crossover design with the fast period as a covariant for the response variable. Covariant analysis revealed that beta-hydroxybutyrate was significantly higher for the ketogenic diet (KD) in the response period compared to standard canine diet (CD) (0.63 mg/dl vs. 0.18 mg/dl). No adverse effects on BUN, creatinine, glucose or other parameters were noted.

In conclusion, it is possible to increase ketone body production in healthy dogs by means of dietary manipulation.

EXAMPLE 2

Materials And Methods 32 obese, adult, cats were tested in a repeated measures design to assess the effect of diet on ketone body production (ketosis) and weight loss.

Prior to the experiment the cats were blocked randomly into two groups based on body condition score and sex. All cats were fed a standard feline maintenance food for 2 weeks prior to the first experimental period. At the start of the first period one group was fed a standard weight reducing diet (Hill's® Prescription Diet® Feline w/d®) and the other group was fed a nutritionally complete ketogenic diet. Both diet types were of the canned type in this dietary trial. All foods were fed ad libitum for period 1 and were then subsequently restricted to 80% of ad libitum intake, as measured in period 1, for period 2 (limit-fed period).

Diet intervention was maintained for 4 weeks of period 1 as ad libitum fed. This was immediately followed by 4 weeks of the limit fed treatment for period 2.

Blood for various analytes was collected at the start and every 2 weeks after the start of the study until the end of period 2. Dual energy x-ray absorptiometry was performed at the beginning and end of each feeding method period.

COMPOSITION OF THE DIET (AS FED BASIS)

| Constituent | Ketogenic Diet | Weight Reducing Diet |
|---|---|---|
| Moisture | 75% | 78% (max) |
| Protein | 9.7% | 10.4% |
| Crude Fiber | 0.5% | 3.1% |
| Crude Fat | 12% | 4.2% |

Minerals and vitamins sufficient to meet daily requirements

Results

Beta-hydroxybutyrate

Cats fed the ketogenic diet had a significantly higher amount of ketosis during both the ad libitum (P<0.001) and feed restricted periods (P<0.0001) compared to the cats on a feline maintenance diet during the prefeeding period. In addition, the cats fed ketogenic diet had significantly higher amounts of ketosis compared to the standard weight-reduction diet during both periods as well (P<0.02). The standard weight-reduction diet did achieve a significant degree of ketosis in the limit-fed period but not during the ad libitum-fed period (P=0.15) as compared to prefeeding values.

BETA-HYDROXYBUTYRATE LEVEL (mg/dl)

| Diet | Pre | End Period 1/Start Period 2 | End Period 2 |
|---|---|---|---|
| Weight reduction diet | 0.39 ± 0.33 | 1.06 ± 0.33 | 2.1 ± 0.33 |
| Ketogenic diet | 0.31 ± 0.33 | 2.64 ± 0.33 | 3.2 ± 0.33 |

Body Mass

Cats fed either diet during either period achieved a significant amount of weight loss compared to the prefeeding period. There was no significant difference between diets during the ad libitum feeding period but the ketogenic diet produced a significantly greater weight loss during the limit fed period (P<0.04).

BODY MASS OF CAT (kg)

| Diet | Pre | End Period 1/Start Period 2 | End Period 2 |
|---|---|---|---|
| Weight reduction diet | 6.3 ± .08 | 6 ± .08 | 5.5 ± .08 |
| Ketogenic diet | 6.1 ± .08 | 5.8 ± .08 | 5.3 ± .08 |

Blood Glucose

Cats fed the ketogenic diet had a significantly decreased concentration of glucose during period 1 compared to the prefeeding concentration. The concentration observed at the end of period 1 was within the normal range for cats but significantly decreased compared to prefeeding values as stated earlier. When diet effects were compared at the end of period 1 and period 2 there was no significant difference measured between diets.

| | BLOOD GLUCOSE (mg/dl) | | |
|---|---|---|---|
| Diet | Pre | End Period 1/Start Period 2 | End Period 2 |
| Weight reduction diet | 112.5 ± 4.7 | 103 ± 4.7 | 106 ± 4.7 |
| Ketogenic diet | 126 ± 4.7 | 108 ± 4.7 | 104 ± 4.9 |

Conclusions

Feeding a high fat, low carbohydrate diet to cats resulted in attainment of a ketotic state, weight loss, and normalization of blood glucose concentrations in obese, adult cats. The ketogenic diet demonstrated comparable improvement in glucose regulation to that previously reported for the weight-loss diet. The ketosis attained was significantly greater than when similar cats were placed on a standard weight reduction diet. In addition, the weight loss attained was similar to that in cats fed a standard weight control diet formulated for cats. No adverse effects of diet were noted in this experimental design. The ketogenic diet demonstrated comparable improvement in glucose regulation in comparison to the results previously reported from use of the standard weight loss diet.

What is claimed is:

1. A method for inducing a state of ketosis in a canine which comprises feeding to a canine in need of such ketosis on a regular basis a diet comprising carbohydrate measured as nitrogen free extract of about 0 to about 20 wt. % of the diet, protein of about 25 to about 70 wt. % of the diet, and fat of about 20 wt. % to about 70 wt. % of the diet on a dry matter basis.

2. The method of claim 1 wherein carbohydrate is from 0 to about 10 wt. % protein is about 25 to about 40 wt. % and fat is about 30 to about 60 wt. %.

3. A method for managing a medical condition or behavior condition selected from the group consisting of seizures, body weight regulation, aggression, obsessive compulsive disorder, separation anxiety, muscle metabolism causing weakness or fatigue, carbohydrate intolerance, disorders of insulin secretion or deficiency, and a combination of any of these conditions in a canine in need of such management which comprises feeding to said canine on a regular basis the diet of claim 1.

4. The method of claim 3 wherein the condition is seizures.

5. The method of claim 3 wherein the condition is body weight regulation.

6. The method of claim 3 wherein the condition is aggressions.

7. The method of claim 3 wherein the condition is obsessive compulsion.

8. The method of claim 3 wherein the condition is separation anxiety.

9. The method of claim 3 wherein the condition is muscle metabolism causing weakness or fatigue.

10. The method of claim 3 wherein the condition is carbohydrate intolerance.

11. The method of claim 3 wherein the condition is insulin secretion or deficiency.

\* \* \* \* \*